United States Patent

Sumiya et al.

Patent Number: 5,870,193
Date of Patent: Feb. 9, 1999

[54] APPARATUS FOR DETERMINING KINDS OF ADSORBATES

[75] Inventors: Atsuhiro Sumiya, Hekinan; Itsuhei Ogata, Anjo; Tsukasa Satake, Ootsu; Juichiro Ukon, Ibaraki, all of Japan

[73] Assignees: Nippon Soken, Inc., Nishio; Horiba, Ltd., Kyoto, both of Japan

[21] Appl. No.: 944,863

[22] Filed: Oct. 6, 1997

[30] Foreign Application Priority Data

Oct. 7, 1996 [JP] Japan .................................. 8-266373

[51] Int. Cl.$^6$ ........................................................ G01B 9/02
[52] U.S. Cl. .................... 356/346; 356/326; 250/339.08; 702/30
[58] Field of Search ................................. 356/346, 326; 250/339.07, 339.08; 702/30

[56] References Cited

U.S. PATENT DOCUMENTS 5,046,846   9/1991   Ray et al. ........................ 250/339.09

FOREIGN PATENT DOCUMENTS 8-248020   9/1996   Japan .

Primary Examiner—Samuel A. Turner
Attorney, Agent, or Firm—Pillsbury Madison & Sutro LLP

[57] ABSTRACT

An infrared spectrometer disperses a radiation ray from a catalyst which has been exposed to a gas for evaluation to adsorb adsorbates thereon, and outputs spectral data in accordance with a wavenumber of the radiation ray to a computer storing reference data. The computer normalizes the spectral data and the reference data, and then, it calculates a product of the normalized spectral data and the reference data. Thereafter, a function of the product is differentiated with respect to the wavenumber to obtain a differential function. Accordingly, a specified wavenumber for which the differential function is zero is determined, so that the common peak of the spectral data and the reference data at the specified wavenumber is accurately determined.

10 Claims, 3 Drawing Sheets

APPARATUS FOR DETERMINING KINDS OF ADSORBATES

CROSS REFERENCE TO RELATED APPLICATION

This application is based upon and claims the benefit of priority of the prior Japanese Patent Application No. 8-266373 filed on Oct. 7, 1996, the contents of which are incorporated herein by reference.

BACKGROUND OF THE INVENTION

1. Field of the Invention

The present invention relates to an apparatus for determining kinds of adsorbates on the basis of spectral data, which is dispersed in accordance with a wavelength or a wavenumber, of an infrared ray, an ultraviolet ray, or the like radiated from the adsorbates.

2. Related Arts

Conventionally, for example, kinds of adsorbates adsorbed on a solid object such as a catalyst are determined on the basis of peaks of spectral data detected by a Fourier transform infrared spectrometer in the following two methods. In a first method, spectral data of materials similar to the adsorbates are collected from various kinds of documents as collection data, and the spectral data obtained from the adsorbates are analyzed by using the collection data. In a second method, at first, materials similar to the adsorbates are experimentally measured by the Fourier transform infrared spectrometer as well to obtain those reference spectral data. Thereafter, the spectral data obtained from the adsorbates are analyzed on the basis of the reference spectral data of the expected materials.

However, the above-mentioned first and second methods need too much time to determine the kinds of the adsorbates. Especially, the first method needs much time to search the spectral data from the documents. In the second method, for example, when various kinds of catalysts carrying adsorbates thereon are analyzed, several times experiments more than the number of the catalysts need to be performed. In addition, a catalyst is usually exposed to a gas so that adsorbates are produced and adsorbed on the catalyst. In this case, even though the gas flowing through the catalyst includes only one component, several kinds of adsorbates may be adsorbed on the surface of the catalyst. Moreover, there is a case where the catalyst is exposed to a mixture gas to observe reactions thereon. In such a case, the number of the adsorbates on the catalyst further increases. Therefore, it is difficult to accurately and efficiently determine the kinds of the adsorbates only by using a commercial database on the basis of a single component.

SUMMARY OF THE INVENTION

The present invention has been made in view of the above-mentioned problems and an object of the present invention is to provide an apparatus capable of accurately and efficiently determining kinds of adsorbates adsorbed on a catalyst or the like.

According to the present invention, a spectrometer disperses a radiation ray radiated from a material, a kind of which is to be determined, and outputs objective spectral data having an intensity in accordance with an optical factor of the radiation ray. On the other hand, reference spectral data is stored in a memory. Normalizing means normalize the objective and reference spectral data. Then, calculating means calculate a product of the intensities of the objective and reference spectral data, and differentiating means differentiate the product. Determining means determine an objective value of the optical factor at which the objective and reference spectral data have a peak, on the basis of the differentiated product.

Accordingly, a common peak of the objective and reference spectral data can be determined. When materials corresponding to peaks of the reference spectral data have been previously proved, according to the present invention, the material corresponding to the peak of the objective spectral data at the objective value of the optical factor can be accurately and efficiently specified. The optical factor may be a wavenumber, a wavelength, or the like. The present invention is suitable for determining kinds of adsorbates adsorbed on a catalyst.

BRIEF DESCRIPTION OF THE DRAWINGS

Other objects and features of the present invention will become more readily apparent from a better understanding of the preferred embodiments described below with reference to the following drawings.

DETAILED DESCRIPTION OF THE PREFERRED EMBODIMENT

Figure 1:
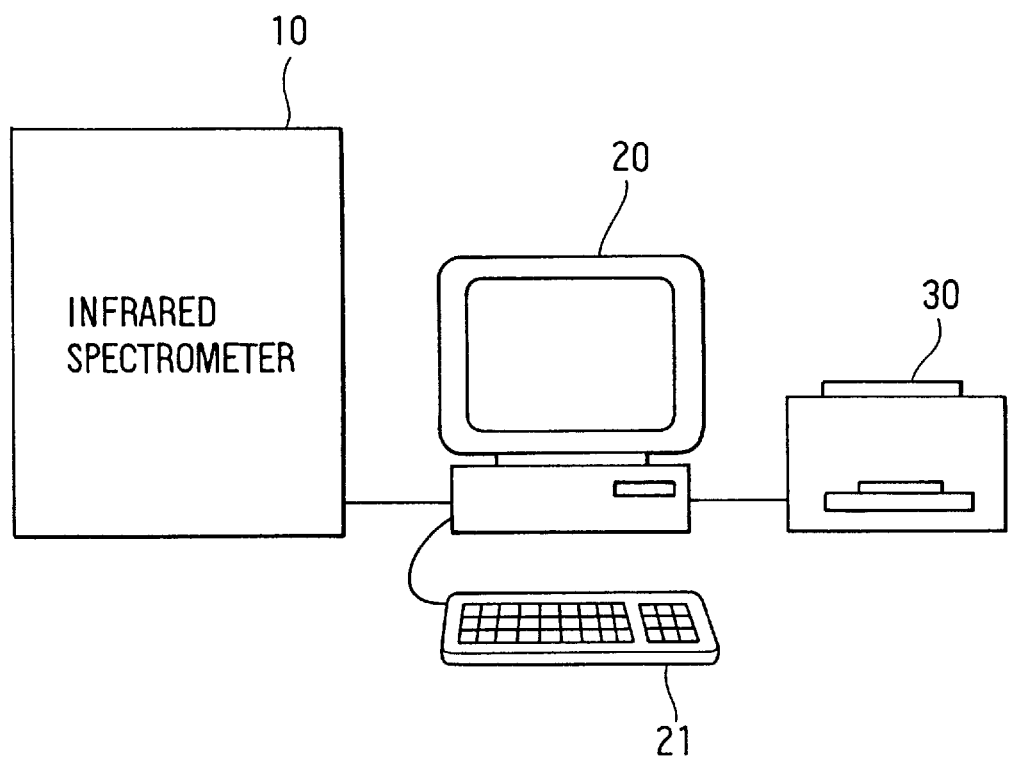
FIG. 1 is a block diagram showing an adsorbate determination system in a preferred embodiment according to the present invention.

A preferred embodiment according to the present invention will be described hereinunder with reference to the drawings. An adsorbate determination system shown in FIG. 1 includes an infrared spectrometer 10, a computer 20, and a recording apparatus 30. The infrared spectrometer 10 disperses an infrared ray radiated from a catalyst carrying adsorbates thereon and outputs the dispersed result to the computer 20 as spectral data.

In the adsorbate determination system, when a heated evaluation gas flows through the catalyst, the adsorbates are adsorbed on the catalyst. The infrared ray is radiated from the thus obtained catalyst and is dispersed by the infrared spectrometer 10. In this embodiment, $PtCa/Al_2O_3$ is employed as the catalyst (hereinafter called "$PtCa/Al_2O_3$ catalyst") and a mixture gas of NO, $C_3H_6$, CO and $O_2$ gases is employed as the evaluation gas. The evaluation gas is heated up to approximately 200° C.

Figure 2:
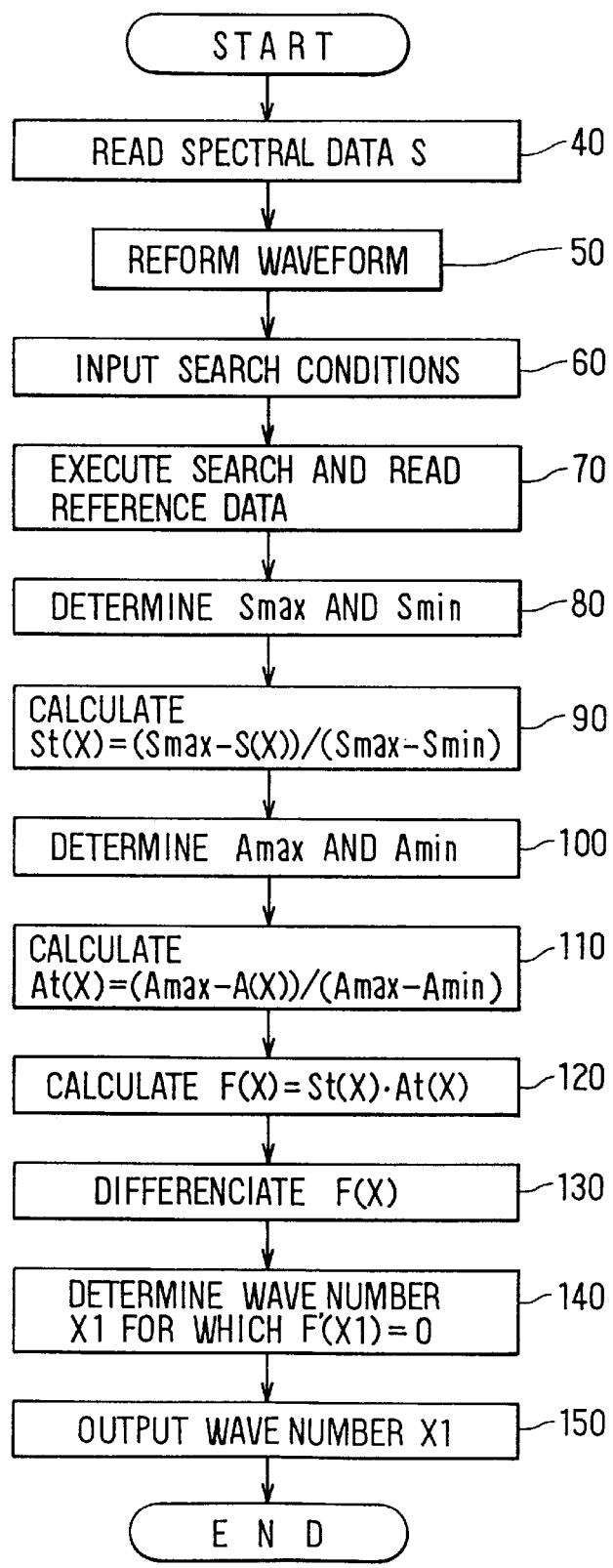
FIG. 2 is a flowchart showing steps for determining kinds of adsorbates by the adsorbate determination system in the embodiment.

The computer 20 is operated via a keyboard 21 to execute computer programs in accordance with a flowchart shown in FIG. 2, thereby processing various calculations. The computer programs have been previously stored in a memory of the computer 20. The recording apparatus 30 prints and records output data of the computer 20.

Figure 3A:
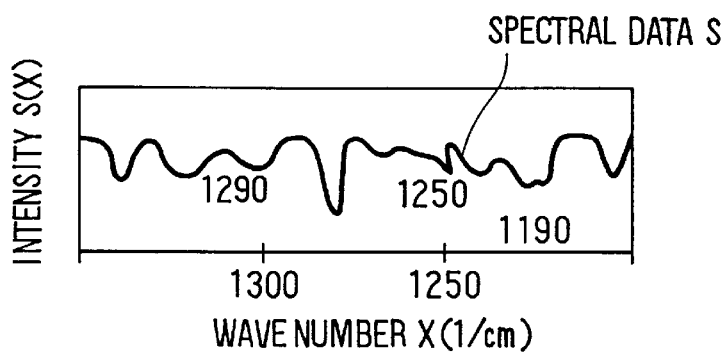
FIG. 3A is a graph showing spectral data S obtained from a catalyst carrying adsorbates thereon to be determined in the embodiment.

Next, the operations of the computer 20 shown in FIG. 2 will be described in more detail. Firstly, the computer 20 starts to execute the computer programs in response to the operation of the keyboard 21 thereof. On the other hand, as mentioned above, the infrared spectrometer 10 disperses the infrared ray radiated from the catalyst carrying the adsorbates and outputs spectral data S to the computer 20. The spectral data S is specified as a spectrum shown in FIG. 3A indicating a relationship between a wavenumber X and an intensity S(X).

In a step 40, the spectral data S is read in the computer 20. Next, in a step 50, the waveform of the spectral data S is reformed to remove noise thereon. Then, in a step 60, search conditions are inputted into the computer 20 by the operation of the keyboard 21. Accordingly, in a step 70, reference data satisfying the search conditions is read out from the computer 20. Plural types of reference data have been previously stored in the memory of the computer 20. Theses reference data can be obtained from a commercial database, results of an experiment, and the like. The reference data need not always be stored in the memory in the computer 20, and may be stored in an external memory.

Figure 3B:
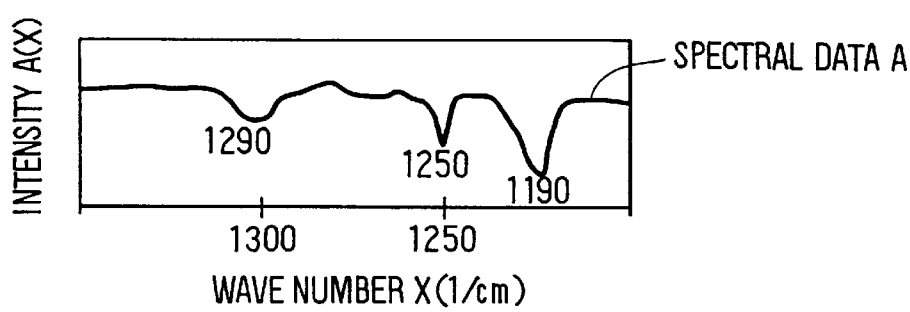
FIG. 3B is a graph showing spectral data A as reference data used in the embodiment.

In this state, the search conditions are inputted into the computer 20 to be satisfied by the reference data obtained from a catalyst similar to the $PtCa/Al_2O_3$ catalyst. Therefore, in this embodiment, spectral data A of a $Pt/Al_2O_3$ catalyst shown in FIG. 3B is read out from the computer 20 as the reference data. The spectral data A is specified as a spectrum indicating a relationship between a wavenumber X and intensity A(X). The spectral data A was obtained by an experiment. In the experiment, a gas having the same composition or containing the same composition as the evaluation gas for the $PtCa/Al_2O_3$ catalyst was used as an evaluation gas. After flowing the evaluation gas through the $Pt/Al_2O_3$ catalyst at the same temperature as that for the $PtCa/Al_2O_3$ catalyst, the thus treated $Pt/Al_2O_3$ catalyst was evaluated by the infrared spectrometer and the result was stored in the memory as reference data.

Figure 3C:
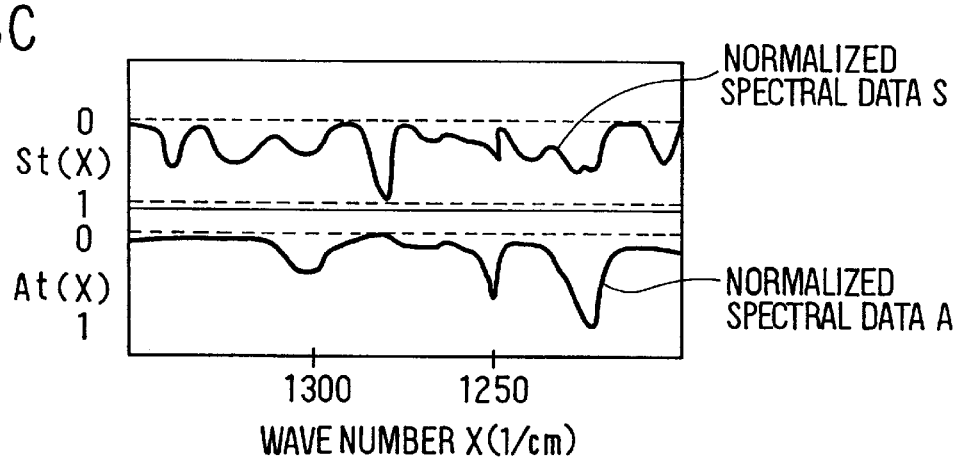
FIGS. 3C and 3D are graphs showing normalized spectral data of the spectral data S and A shown in FIGS. 3A and 3B.

After the search, in a step 80, concerning the spectral data S, the maximum intensity Smax and the minimum intensity Smin are determined from the intensity S(X). In a next step 90, a normalized intensity St(X) (refer to FIG. 3C) is calculated from S(x), Smax, and Smin by using the following formula (1);

$$St(X) = (Smax - S(X))/(Smax - Smin) \quad (1)$$

In a step 100, concerning the spectrum data A, the maximum intensity Amax and the minimum intensity Amin are determined from the intensity A(X) as well. In a next step 110, a normalized intensity At(X) (refer to FIG. 3C) is calculated from A(X), Amax, and Amin by using the following formula (2);

$$At(X) = (Amax - A(X))/(Amax - Amin) \quad (2)$$

In this way, the spectral data S and A are normalized. Thereafter, in a step 120, the product of St(X) and At(X) is calculated, so that a function F(X) is obtained. That is, the function F(X) is represented by the following formula (3);

$$F(X) = St(X) \cdot At(X) \quad (3)$$

Next, in a step 130, the function F(X) is differentiated with respect to X, so that a first differential function F'(X) is obtained. In a step 140, wavenumbers X1 for which the first differential function F'(X1)=0 are determined. For the wavenumber X1, the function F(X1) has the maximum values. Then, in a step 150, the wavenumbers X1 are outputted to the recording apparatus 30.

Figure 3D:
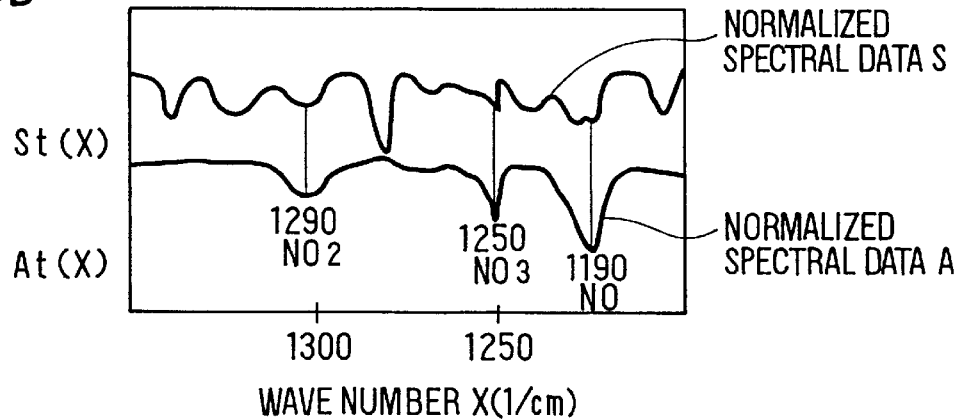

Accordingly, it is accurately confirmed that both of the normalized intensities St(X) and At(X) of the spectral data S and A have peaks at the wavenumbers X1. That is, the common peaks of the intensities S(X) and A(X) of the spectral data S and A can be accurately determined. Specifically, concerning the spectral data S and A respectively obtained from the $PtCa/Al_2O_3$ and $Pt/Al_2O_3$ catalysts, as shown in FIG. 3D, the wavenumbers X1 for which the first differential function F'(X1)=0 are 1190 $cm^{-1}$, 1250 $cm^{-1}$, and 1290 $cm^{-1}$ and both of the spectral data S and A have the peaks at the wavenumbers of 1190 $cm^{-1}$, 1250 $cm^{-1}$, and 1290 $cm^{-1}$.

Here, it has been previously proved that the spectral data A has the peaks at the wavenumbers of 1190 $cm^{-1}$, 1250 $cm^{-1}$, and 1290 $cm^{-1}$ respectively peculiar to adsorbates of NO, $NO_3$, and $NO_2$. Accordingly, it is determined that the spectral data S has the peaks peculiar to the adsorbates of NO, $NO_3$, and $NO_2$.

That is, it can be determined that the $PtCa/Al_2O_3$ catalyst has the adsorbates of NO, $NO_3$, and $NO_2$. Thus, according to the present invention, the kinds of the adsorbates on the $PtCa/Al_2O_3$ catalyst can be easily and accurately determined. In the present invention, because the wavenumbers X1 are obtained from the first differential function F'(X), faulty judgement of the peak of the spectral data S does not occur.

Although the spectral data A obtained from the $Pt/Al_2O_3$ catalyst is used as the reference data in this embodiment, the reference data can be obtained by using catalysts of $PtBa/Al_2O_3$, $PtNa/Al_2O_3$, $PtK/Al_2O_3$, and the like. Further, although each of the spectral and reference data indicates characteristics of an intensity in accordance with a wavenumber of a radiation ray in this embodiment, each of the spectral and reference data may indicate characteristics of the intensity in accordance with a wavelength of the radiation ray. Further, the present invention can be applied not only to the adsorbate determination system including the infrared spectrometer 10 but to the other adsorbate determination systems, for example, including a spectrophotometer for ultraviolet and visible region.

While the present invention has been shown and described with reference to the foregoing preferred embodiment, it will be apparent to those skilled in the art that changes in form and detail may be made therein without departing from the scope of the invention as defined in the appended claims.

What is claimed is:

1. An apparatus for determining a kind of material, the apparatus comprising;
    a spectrometer for dispersing a radiation ray radiated from the material and outputting objective spectral data having an intensity in accordance with an optical factor relative to the radiation ray;
    a memory for storing reference spectral data:
    normalizing means for normalizing the objective and reference spectral data;
    calculating means for calculating a product of intensities of the normalized objective and reference spectrum data;
    differentiating means for differentiating the product; and
    determining means for determining an objective value of the optical factor, at which the objective spectral data and the reference spectral data has a peak, on the basis of the differentiated product.

2. An apparatus for determining a kind of material according to claim 1, wherein:
    the product is a function of the optical factor; and
    the differentiated product is a differential function of the optical factor, and is zero for the objective value of the optical factor.

3. An apparatus for determining a kind of material according to claim 1, wherein:

the reference spectral data has reference peaks peculiar to specified materials at specific values of the optical factor, the specific values including the objective value; and the objective spectral data has a peak peculiar to one of the specified materials at the objective value of the optical factor.

4. An apparatus for determining a kind of material according to claim 1, wherein the material is an adsorbate.

5. An apparatus for determining a kind of material according to claim 4, wherein the adsorbate is adsorbed on a catalyst.

6. An apparatus for determining a kind of material according to claim 1, wherein the optical factor is a wavenumber of the radiation ray.

7. An apparatus for determining a kind of material according to claim 1, wherein the optical factor is a wavelength of the radiation ray.

8. A method for determining a kind of an objective material, comprising of:

storing reference spectral data, the reference spectral data having an intensity in accordance with an optical factor relative to a reference radiation ray from a reference material;

detecting a objective radiation ray radiated from the objective material;

outputting objective spectral data in accordance with the objective radiation ray, the objective spectral data having an intensity in accordance with the optical factor relative to the objective radiation ray;

normalizing intensities of the reference spectral data and the objective spectral data;

calculating a product of the normalized intensities of the reference spectral data and the objective spectral data, the product being a product function of the optical factor;

differentiating the product function with respect to the optical factor, the differentiated product function being a differential function of the optical factor; and determining a specific value of the optical factor for which the differential function is zero.

9. A method according to claim 8, wherein the optical factor is a wavenumber of the radiation ray.

10. A method according to claim 8, wherein the optical factor is a wavelength of the radiation ray.

* * * * *